US00RE35631E

United States Patent [19]

Fraschini et al.

[11] E Patent Number: Re. 35,631

[45] Reissued Date of Patent: Oct. 14, 1997

[54] METHOD OF PRODUCTION OF ESSENTIALLY PURE MELATONIN AND THE METHOD OF SOLUBILIZING MELATONIN IN WATER

[75] Inventors: Franco Fraschini; Luigi Di Bella, both of Milan; Ermanno Duranti, deceased, late of Milan; Maria Teresa Moni Duranti, legal representative, Urbino; Andrea Duranti, legal representative, Urbino; Lucia Duranti, legal representative, Urbino, all of Italy

[73] Assignee: IFLO S.A.S., Milan, Italy

[21] Appl. No.: 252,905

[22] Filed: Jun. 2, 1994

Related U.S. Patent Documents

Reissue of:

[64] Patent No.: 5,122,535
Issued: Jun. 16, 1992
Appl. No.: 312,627
Filed: Feb. 17, 1989

[30] Foreign Application Priority Data

Feb. 25, 1988 [IT] Italy ..... 19549 A/88
Sep. 8, 1988 [IT] Italy ..... 21872 A/88

[51] Int. Cl.[6] ..... C07D 209/16; C07D 473/34; A61K 31/40; A61K 31/52

[52] U.S. Cl. ..... 514/415; 514/46; 536/27.6; 548/504; 548/507

[58] Field of Search ..... 544/276; 514/46, 514/415; 548/504, 508, 507; 536/27.3

[56] References Cited

U.S. PATENT DOCUMENTS 2,248,155 6/1941 Zellner ..... 548/502
2,416,258 2/1947 Jenkins et al. ..... 548/504
3,947,584 3/1976 Zirngibl et al. ..... 424/274

OTHER PUBLICATIONS

Kirk–Othmer, "Encyclopedia of Chemical Technology, 2nd ed., " vol. 4 (1964), pp. 149–153.

Fessenden and Fessenden, "Organic Chemistry" (1982) pp. 624, 670–672, 714–716.

Robert L. Grob, ed. "Modern Practices of Gas Chromatography" (1977) pp. 611–613.

Katritzky, ed. "Comprehensive Heterocyclic Chemistry" (1984) pp. 334–338.

Houlihan, ed. "Indoles, Part Three," (1979) pp. 12–20.

*Primary Examiner*—Matthew V. Grumbling
*Attorney, Agent, or Firm*—Bucknam and Archer

[57] ABSTRACT

A method of synthesizing an indole derivative of the tryptamine type particularly [melatonine,] *melatonin* comprising the steps of 1) reacting potassium phthalimide and 1,3-di-bromopropane to obtain 3-bromopropylphthalimide; 2) reacting 3-bromopropylphthalimide with sodium acetoacetic ester in ethanol to obtain ethyl-2-acetyl-5-phthalimidopentanoate; 3) reacting the product from step 2) with diazo-p-anisidine to obtain 2-carboxyethyl-3-(2-phthalimidoethyl)-5-methoxy-indole; 4) reacting the 2-carboxyethyl-3-(2-phthalimidoethyl)-5-methoxy-indole with 2N/NaOH and then 20% $H_2SO_4$ to obtain impure 5-methoxytriptamine, which is purified by means of hexamethyldisilazane. The mono and disubstituted derivatives are obtained and the monosubstituted derivative is hydrolyzed with aqueous methanol and then recrystallized from ethanol. The N-acetyl derivative is prepared by reaction with acetic anhydride. [Melatonine] *Melatonin* of high purity is obtained for prophylaxy and also against AIDS (Acquired Immuno Deficiency Syndrome).

6 Claims, 1 Drawing Sheet

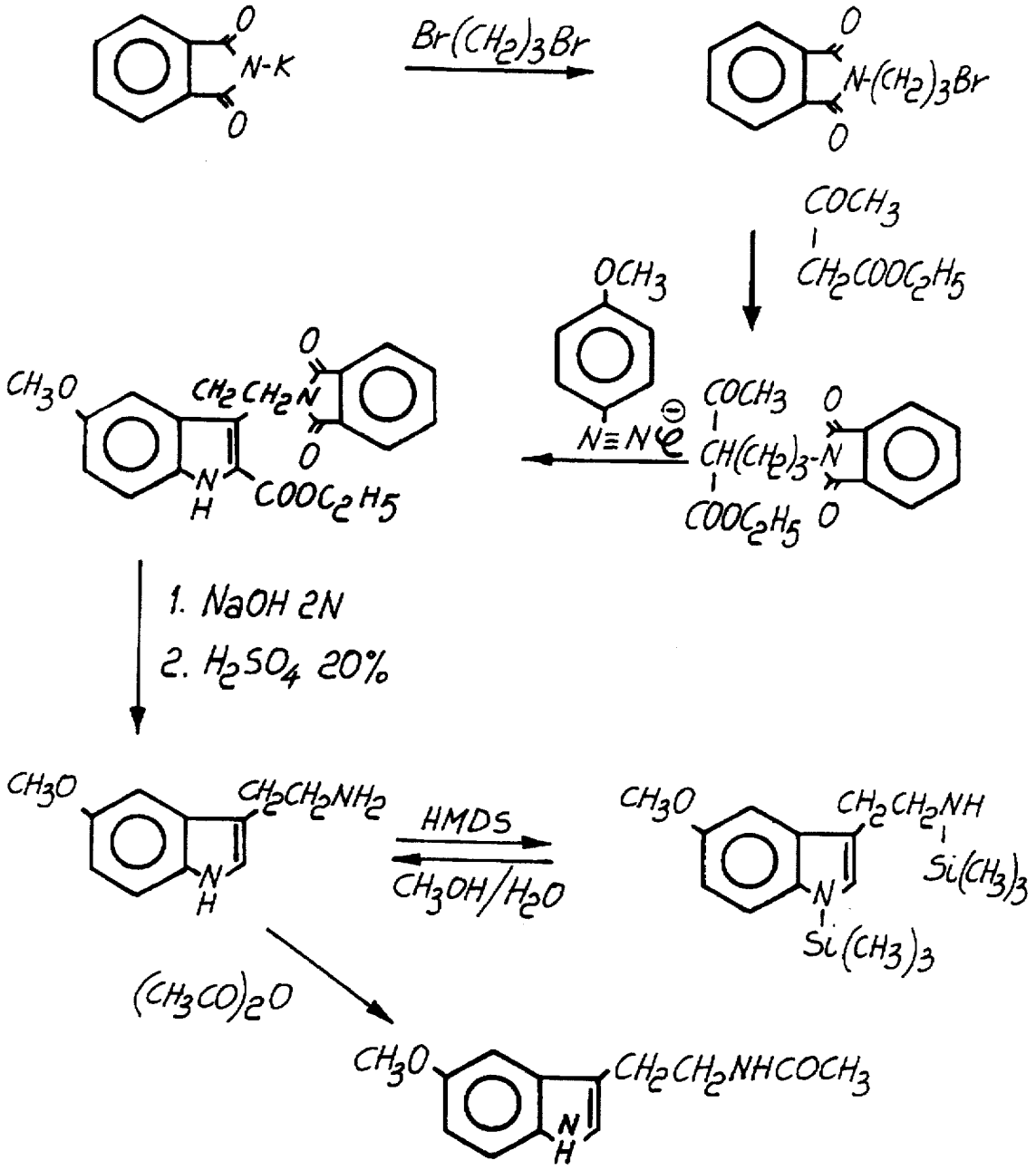
N-K
Br(CH2)3Br
N-(CH2)3Br
COCH3
CH2COOC2H5
OCH3
N≡N⊖
COCH3
CH(CH2)3-N
COOC2H5
CH3O
CH2CH2N
COOC2H5
1. NaOH 2N
2. H2SO4 20%
CH3O
CH2CH2NH2
HMDS
CH3OH/H2O
CH3O
CH2CH2NH
Si(CH3)3
Si(CH3)3
(CH3CO)2O
CH3O
CH2CH2NHCOCH3

METHOD OF PRODUCTION OF ESSENTIALLY PURE MELATONIN AND THE METHOD OF SOLUBILIZING MELATONIN IN WATER

Matter enclosed in heavy brackets [ ] appears in the original patent but forms no part of this reissue specification; matter printed in italics indicates the additions made by reissue.

BACKGROUND OF THE INVENTION

The present invention relates to a total synthesis method for preparing an indole structure derivative product class, of the tryptamine type, in particular of [melatonine] *melatonin* or N-acetyl-5-methoxytriptamine type, having a high purity degree and easily soluble, for therapeutic use against acquired immuno-deficiency syndromes or so-called AIDS.

As is known, it has been found that [melatonine] *melatonin* (MTL), administered with suitable doses and at given times, is able of reducing proteic synthesis of hypothalamus and hypophisis and that it, moreover, may inhibit the synthesis of gonadostymulines.

Such an action is probably exerted by means of a modulation of genic transcription and repression, as well as on the incretion of the two GH and PRL growth factors, under particular conditions.

The above mentioned overall effects, which are associated with other particular actions, as disclosed in a more detailed way hereinafter, justify as useful, even if not indispensable, the use of [melatonine] *melatonin* against tumours.

In fact one may reasonably think that [melatonine] *melatonin* pertains to that class of drugs which interfere with the growth of neoplastic cells and reduce the life time thereof.

On the other hand, also known is the fact that presently available methods for making the tryptamine structure having the hydrogen atom at the 5-position replaced by the group $OCH_3$, are based on a series of chemical reactions providing 2-carboxyethyl-3-(2-phthalimidoethyl)-5-methoxy-indole, therefrom there is obtained 5-methoxytryptamine by means of a plurality of comparatively complex and low yield processing steps.

More specifically, known prior art methods comprise an alkaline saponifying step providing 2-carboxy-3-(2-O-carboxybenzamidoethyl)-5-methoxy-indole acid which is then dry decarboxylated at 250° C. in order to form phthalimidoethyl-5-methoxy-indole, which is then water hydrazinolized to provide 5-methoxytryptamine.

In order to obtain pure N-acetyl-5-methoxytryptamine or [melatonine] *melatonin* with a high yield, it is necessary to have a high purity starting product, that is 5-methoxytryptamine.

Known conventional purifying methods, based on the use of solvents or mixtures thereof, on the other hand, have not provided a sufficiently high purity degree with a contemporaneous high production yield.

SUMMARY OF THE INVENTION

Accordingly, the main object of the present invention is to overcome the above mentioned drawback by providing a method for making, with high production yields, very pure 5-methoxytryptamine, which method essentially comprises a synthesis known per se with respect to the reagents, but carried out by new techniques starting from 2-carboxyethyl-3-(2-phthalimidoethyl)-5-methoxy-indole.

Another object of the invention is to provide such a method which, in addition to simplifying the processing steps, can provide [melatonine] *melatonin* starting both from 5-methoxytryptamine, in raw form, and from pure 5-methoxytryptamine.

Yet another object of the present invention is to provide a total synthesis method which provides a very pure and reliable product, with consistent curative properties.

According to one aspect of the present invention, the above mentioned objects, as well as yet other objects, which will become more apparent hereinafter, are achieved by a total synthesis method for making an indole structure derivative product class, of the tryptamine type, in particular of [melatonine] *melatonin* or N-acetyl-5-methoxytryptamine type, having a high purity degree and easily water soluble for therapeutic use against acquired immuno-deficiency syndromes comprising the steps of combining potassium phthalimide and dibromopropane, to form 3-bromopropylphthalimide, adding [acetacetic] *acetoacetic* ester in the presence of anhydrous ethanol dissolved sodium to form ethyl-2-acetyl-phthalimidopentanoate, adding diazo-p-anisidine to form 2-carboxyethyl-[3-(2-phtalimidoethyl)-]*3-2-phthalimidoethyl*-5-methoxy-indole, which is processed, in a first step, by NaOH 2N up to a complete solution and, then, by $H_2SO_4$ (at 20%) to form raw 5-methoxytryptamine, which is purified by means of hexamethyldisilazane, so as to form the related mono- and bi-derivative therefrom, by means of an aqueous methanol hydrolysis, there is obtained [the starting compound] *5-methoxytryptamine.*

BRIEF DESCRIPTION OF THE DRAWING

Further characteristics and advantages of the present invention will become more apparent from the following detailed description of the total synthesis method according to the invention, with reference to the chemical diagram shown in the accompanying drawing table.

DESCRIPTION OF THE PREFERRED EMBODIMENT

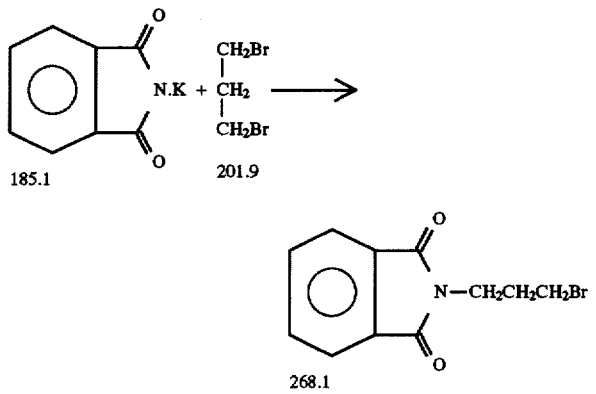

The method according to the invention comprises the step of preparing 3-bromopropylphthalimide as follows: into a 3-neck 1-liter flask, provided with stirrer and cooling medium, there are introduced 101 g (0.5 moles) of 1.3-dibromo-propane, 250 ml acetone and 15 g K-phthalimide, by reflux processing the mixture under stirring. At 1 hour time intervals there are added further (15+10+6.3) g K-phthalimide (46.3 g corresponding to 0.25 moles), by holding under reflux conditions for a total period of 24 hours.

At the end of this period the precipitated KBr is filtered and acetone is evaporated in a rotary evaporating device: the obtained oil is distilled under vacuum (as provided by a water pump) and there are recovered 48.5 g (0.25 moles) of 1,3-dibromopropane, which is distilled at 69°–70° C. The residue (dissolved before solidification in the distillation flask) is [crystalized] *crystallized* twice from ethanol, so as to remove the small amount of formed diphthalimidopropane.

There are thus obtained 48.2 g of a white [crystaline] *crystalline* solid, melting point 72° C., with a yield of 72%.

Purity is controlled for TLC on silica gel, using as eluent benzene-acetone (45:5), freshly prepared, Rf of about 0.95 (diphthalimidopropane having a lower Rf).

By analogous, reactions, in which K-phthalimide is added once, there is obtained a product which contains greater amounts of diphthalimidopropane, thereby it is necessary to purify by distillation (e.g. 150° C./0.25 mm) by using a Vigreux device without cooling, since the distillate tends toward solidification. The yield is substantially equal to the above disclosed yield.

[Preparing] *Preparation* of ethyl-2-acetyl-5-phthalimidopentanoate

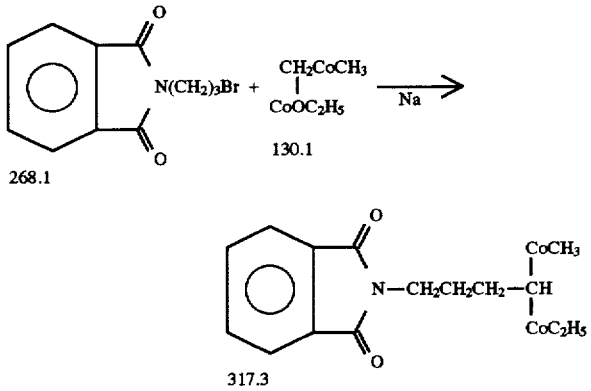

In a three-neck flask having a capacity of 500 ml, provided with $CaCl_2$ cooling there are dissolved 4.60 g (0.2 g/A) Na in 100 ml anhydrous ethanol. To the solution, at room temperature, there are added 27.32 (0.21 moles) of [acetacetic esther] *acetoacetic ester* and then, after ten minutes, 40 g of 3-bromopropylphthalimide and, after one hour, further 12.5 g (in total 52.5 g corresponding to 0.196 moles), by holding the reflux processing and continuing for further three hours.

At the end of this period, sodium bromide is filtered, the solution is neutralized by 2N HCl and ethanol is evaporated under reduced pressure. The residue is recovered by ether, washed by $H_2O\times2$, dried on anhydrous $Na_2SO_4$ and the solvent is evaporated, thereby providing a light yellow oil which is [crystalized] *crystallized* by dissolving it in a minimum ethanol amount by adding a small amount of ether and upon [ageing] *aging* for a night.

There are thus obtained 45 g (yield 72%) of a white crystalline solid, with m.p. 60° C. Upon [recrystalisation] *recrystallization* there is obtained a m.p. of 63° C. Product also [crystalizes] *crystallizes* from benzene-petroleum ether.

TLC on silica gel, benzene-acetone (45:5), Rf about 0.70.

Purification of 4-anisidine

A sample of 4-anisidine, of a very dark colour, is dissolved in an excess of 2N HCl and the solution is repeatedly extracted by chloroform as far as the colour is no longer extracted.

The acid solution is boiled [by] *with* decolorizing charcoal and hot filtered. The strongly cooled filtrate is processed by concentrated NaOH and extracted by chloroform. The chloroform solution is dried on anhydrous $Na_2SO_4$ and evaporated under reduced pressure. The residue is [crystalized] *crystallized* from benzene thereby providing a white lamellae product with a melting point of 57° C.

[Preparing] *Preparation* of 2-carboxyethyl-5-(2-phthalimidoethyl)-5-methoxy-indole

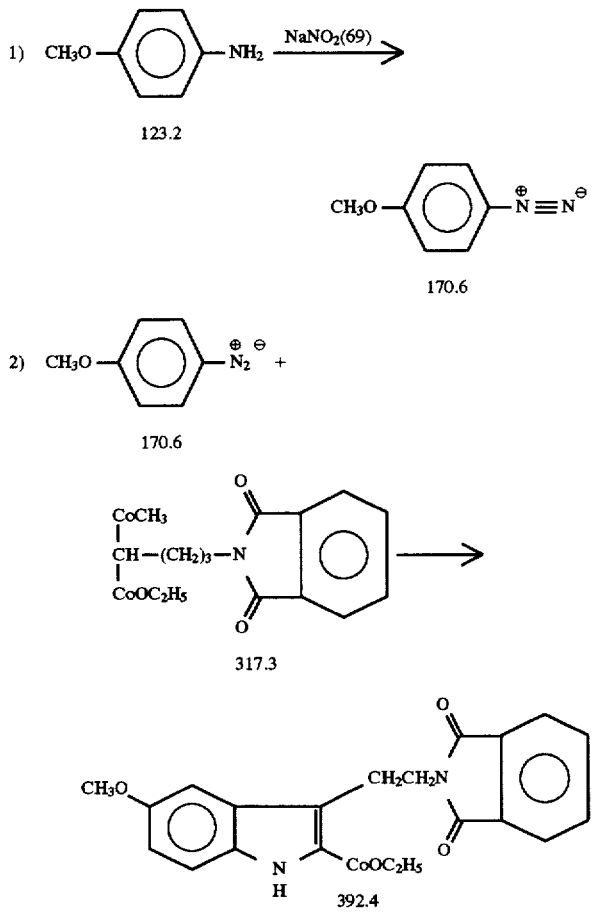

24.64 g (0.2 moles) p-anisidine in 80 ml ethanol 120 ml water and 80 ml (0.96 moles) 37% HCl are diazotized at 0°–5° C. by 14.5 g (0.21 moles) $NaNO_2$ in 40 ml water; at the end the reaction is continued for other 30 minutes at the same temperature.

The thus obtained diazonium salt solution is added to a solution (stirred and held at 0° C.) of 63.46 g (0.2 moles) of ethyl-2-acetyl-5-phthalimidopentanoate and of 130.64 g (0.96 moles) of sodium acetate trihydrate in 700 ml ethanol. The reaction is continued for 1 hour (the end pH must be included in the 5–6 range); then the solution is brought to room temperature under stirring for other three hours.

At the end of this period, the mixture is diluted with 2 l water and extracted by $CH_2Cl_2$ three times; the organic phase, after washing by water and drying on anhydrous $Na_2SO_4$, is evaporated, thereby providing 89.2 g of a dark red oil which is dissolved in a minimum amount of ethanol and introduced into a 3-neck 1 liter capacity flask, provided with stirrer, cooler and loading funnel. By stirring and heating there are added in 20 minutes 480 ml of a 10% solution of gaseous HCl in ethanol, by refluxing for 2 hours.

At the end of this period, the mixture is cooled down (for a night in a refrigerator or for 3 hours in an ice bath) and filtered by fully washing with methanol, water and methanol again. The dry solid material has a weight of 57.3 g (yield 73%), with a m.p. of 234°–7° C.

By [recrystalisation] *recrystallization* from glacial acetic acid there are obtained 54.9 g (yield 70%) with m.p. 239°–40° C.

TLC on silica gel, concentrated benzene-methanol-ammonia (50:10:1), Rf about 0.80.

[Preparing] *Preparation* of 5-methoxytryptamine

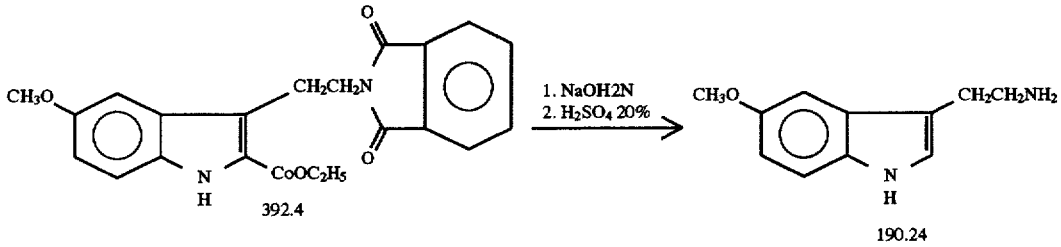

Into a 3-neck 3 liter flask, provided with stirrer, cooler and loading funnel, there are introduced 58.86 g (0.15 moles) of 2-carboxyethyl-3-2-phthalimidoethyl-5-methoxy-indole and 187.5 ml (15 g; 0.375 moles) of 2N NaOH and the mixture is refluxed at 135° C. for 2.5 hours, thereby providing a complete solution.

By holding stirring and temperature, there are added, in 30 minutes, 750 ml of $H_2SO_4$ (at 20%) (v/v), by further reflux processing for 4 hours.

At the end, the solution is cooled (for a night in a refrigerator or for 3 hours in an ice bath), by removing by filtration the precipitated [phtalic] *phthalic* acid. The solution is made alkaline by cooling with 30% NaOH and extracted by $CH_2Cl_2$×3; the collected extracted materials are washed with water, dried on anhydrous $Na_2SO_4$ and evaporated, thereby providing 20.25 g (yield 71%) of crude 5-methoxytryptamine.

TLC on silica gel, sat. $CHCl_3$, $NH_4OH$-methanol (50:2), Rf about 0.65.

[Purifying] *Purification* of 5-methoxytryptamine

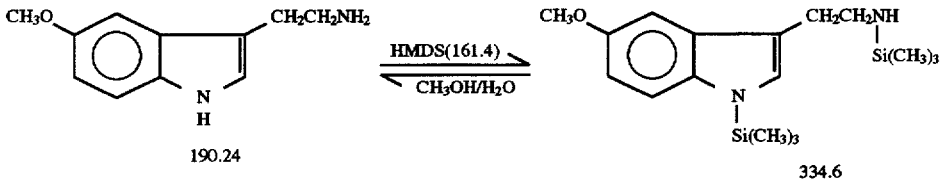

To purify 5-methoxytriptamine, 19 g (0.1 moles) of 5-methoxytriptamine (in a raw condition) and 76 ml (58.86–0.36 moles) of hexamethyldisilazane are refluxed for a night in a flask with sodium hydroxide protected cooling.

The solution is firstly distilled under normal pressure for recovering excess HMDS (43.6 g; 0.27 moles; m.p. 124°–5° C.) and then under a reduced pressure, thereby providing a mixture of biderivative (20.26 g; m.p 135°–40° C. at 0.1 Torr) and monoderivative material (5.25 g; m.p. 165° C. at 0.1 Torr).

The silyl derivative is [hydrolized] *hydrolyzed* by aqueous methanol, thereby providing 15.36 (0.08 moles) with a yield of 80%. The mixture is [crystalized] *crystallized* from ethanol, so as to provide a white product having a m.p of 120°–1° C.

[Preparing] *Preparation* of N-acetyl-5-methoxytryptamine

Method A

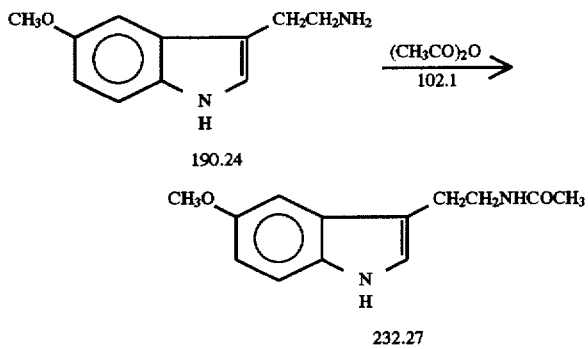

To a suspension, cooled in ice, of 20 g (0.105 moles) of pure 5-methoxytryptamine in 400 ml methylene chloride there is slowly added, under stirring, a cold solution of 20 ml (0.21 moles) of acetic anhydride in 200 ml methylene chloride. Stirring and cooling are continued for 1 hour (the reaction progression can be controlled by TCL) so as to obtain a [full] *complete* solution; then the solution is washed with $Na_2CO_3$×2, under long stirring, and then with water. The organic phase, dried on $Na_2SO_4$ and evaporated, provides 24 g (yield 98%) of lightly colored [melatonine] *melatonin*.

In order to obtain a white product it is sufficient to process, if necessary, by charcoal in acetone and then [crystalize] *crystallize* from acetone-water. There are obtained 20 g (yield 83%) with m.p 116°–7° C. (Tottoli).

TLC on silica gel, chloroform-ethanol (9.1). Rf of about 0.60.

Yield 46.5%, calculated on 2-carboxyethyl-3-(2-phthalimidoethyl)-5-methoxy-indole.

Method B

To a suspension, cooled in ice, of 5 g (26.3 moles) of 5-methoxytryptamine (in a raw condition) in 100 ml methylene chloride there is slowly added, under stirring, a cold solution of 5 ml (52.6 moles) of acetic anhydride in 50 ml of methylene chloride. Stirring and cooling are continued for 1 hour (the reaction progression can be controlled by TLC), so as to obtain a [full] *complete* solution; then the solution is washed by $Na_2CO_3$ 2N×2, under strong stirring, and then by water. The organic phase, dried on anhydrous $Na_2SO_4$ and evaporated, provides 6 g of [raw melatonine,] *crude melatonin* which is purified by chromatography on column (4 cm; diameter/length ratio 1:5) of Merck silica gel (70–230 mesh) (120 g); the solution is eluted by methylene chloride in order to remove the scarcely polar products thereby providing pure [melatonine] *melatonin* by eluting with methylene chloride-acetone (8.2). There are obtained 4 g of product (purifying yield 65%) which are [crystalized] *crystallized* from acetone-water. Melting point 116°–7° C.

TLC on silica gel, chloroform-ethanol (9:1), Rf of about 0.60.

Yield of 46% calculated on 2-carboxyethyl-3-(2-phtalimidoethyl)-5-methoxy-indole.

In order to better disclose the total [synthesis] *synthetic* method according to the present invention, reference is now made to the accompanying drawing, in which there is shown the diagram of the several steps of this method.

The thus obtained [melatonine] *melatonin* has such a purity that it can be used, in suitable packages, both in the tumoural prophylaxis and in the tumoural therapy, as well as against AIDS.

In fact it has been found that this product, administered in suitable doses and with suitable procedures, provides, in addition to the above mentioned effects, also specific effects, such as:

a calming and slightly hypnotic action (which is useful for improving the antipain effect) and an antispasm effect (which is indispensable in the therapy of primitive tumours and brain metastasis tumours);

a mielotropic action, thereby it is possible to use comparatively high doses of radiation and chemical therapeutical substances;

an antimitotic action, perhaps of the same type of those found on the microtubule arrangement and eyelash regeneration;

a modulating action on the NK cell activity.

In this connection it should be pointed out that, in order to obtain the above mentioned effects, there are sufficient very small doses by os or by i.m injection or endovenous injection: from 2 mg/day to 20 mg/day; higher doses should be avoided in order to prevent the antiaggregating action of [melatonine] *melatonin* on the circulating platelets.

In addition there has been recently found a possible relationship between opium peptides and the action mode of [melatonine] *melatonin*.

This fact is very important, since antagonists are able of slowing neoplastic growth, whereas opium agonists seem to have an antimithotic action, both in vivo and in vitro.

In particular, [melatonine] *melatonin* has been found to be of essential importance in the following cases:

neuroblastoms, glioblastoms and astrocytoms;

leio and rabdomions;

condro-osteo-mixo-liposarcomas;

melanomas;

tumours of the respiratory paths and lungs:

tumours of the digestive apparatus;

tumours of the man and woman genital apparatus, loins, and prostate;

spino and basocellular epitheliomas:

malignant lymphomas and, with a less efficacy, in the Hodgkin lymphoma;

plasmocytoms;

thyroid tumours;

[mamma] *mammary* tumours;

linphoblastic leukaemia and cronic limphoides;

mieloblastic leukaemia and cronic mieloid.

Thus, we can reasonably think that the efficacy of [melatonine] *melatonin* in the above very different nature tumours is such as to advise its use [it] because of its general indirect and not specific action, which, on the other hand, is very essential.

In this connection it should be moreover pointed out that in the last ten years, experimental reports have stressed the fact that the [neuroendocrin] *neuroendocrinologic* system and immunity seem to be mutually related and that some diseases, characterized by immunitary disorders, may be due to alterations of this interrelationship.

Among the several modulating [neuroendocrin] *neuroendocrinologic* factors affecting the immunitary system pineal secretions and endogen opium peptides seem to have a very important function.

In fact there has been demonstrated that both pineal gland and opium system are involved in the control of cellular growth and tumoural growth.

At the immunitary system level, the endogen opium peptides seem to provide a stimulating-action; in particular endorphine may, under given conditions, stimulate the NK activity and the interleukine production.

On the other hand, basic data seem to suggest that [melatonine] *melatonin*, i.e. N-acetyl-5-methoxytryptamine has a very important function in maintaining an efficient [immunologic] *immunological* response in rats, under induced immunitary experimental stimulation.

The effect provided by [melatonine] *melatonin*, under the disclosed experimental conditions, is hindered by the simultaneous administration of naltrexone; this suggests that the immunomodulating action of [melatonine] *melatonin* can be controlled by opium mechanisms.

Under basal condition and in the absence of the immunity activity, in rats, the [melatonine] *melatonin* administration has no efficacy.

There has been moreover demonstrated that repeated administrations of pineal extracts induce lymphocytopoiesis and timic hyperplasia, whereas pinealhectomy causes timic atrophy.

In this connection it should moreover be stressed that pineal [endocrin] *endocrinologic* function itself seems to be modulated by opioid tone and that, vice versa, some typical actions of opium substances, such as analgesic action, are controlled by the activity of pineal gland and follow a [circadic rythm] *circadian rhythm.*

Thus, one may reasonably think that the pineal gland, through its main [melatonine] *melatonin* hormone, as a structure involved into the modulation of the [neuroendocrin] *neuroendocrine* activities, is able of controlling the effects exerted by phychoemotional effects on the immunitary system.

In fact, documented [circadic] *circadian* variations of the NK activity could be related to the [circadic rythm] *circadian rhythm* of [melatonine] *melatonin*, as demonstrated by some recent results.

From a lot of experimental tests, it has been found that surprising results has been obtained in the treatment of patients affected by AIDS.

These patients have been treated [by melatonine] *with melatonin* with doses of 20 mg per day and, after a long therapy, it has been demonstrated that they had a less amount of infections, with a significative increase of the "null cells", as determined by an examination of peripheral blood.

[Melatonine] *Melatonin*, or N-acetyl-5-methoxytryptamine, which has a formulation which constitutes the subject matter of the Italian Patent Application No. 23,323 A/79 in the name of the same [applicant] *applicants*, and which [his] *is* herein included by reference, has been found to provide significative improvements in the treatment of patients affected by AIDS.

The effect of [melatonine] *melatonin* is further increased as [melatonine] *melatonin* is used together with azidotimidine.

In particular, patients affected by AIDS, who were treated by azidotimidine with a dose of 3 mg/kg each four hours, and who required weekly blood transfusions because of the alteration of the coagulation processes, and subjected to a simultaneous treatment by [melatonine] *melatonin*, with a dose of 20 mg per day, provided greatly improved collateral effects affording the possibility of performing blood transfusions at 8 week intervals.

These patients have been treated [by melatonine] *with melatonin*, with the mentioned doses of 20 mg per day, and after a long therapy it has been demonstrated that they had a less amount of infections, with a significative increase of the null cells, as determined by an examination of peripheral blood.

Thus it has been found that [melatonine] *melatonin* can efficiently treat patients affected by AIDS, mainly in combination with other known treatment methods.

In this connection, it should be apparent that all of the administering details and the used doses can be suitably changed depending on each patient.

In particular, for a better use of [melatonine,] *melatonin* the present invention suggests to solubilize it [with] *in* water in order to facilitate the therapeutical applications, by using a particular method.

In fact, as is known [melatonine] *melatonin* is a substance scarcely soluble in water, and satisfactorily soluble at 40°–45° C.

After long experimentation applicant has found that adenosine is adapted to easily dissolve [melatonine] *melatonin* in water.

In particular an optimal ratio has been found i.e.:

for a mole of [melatonine] *melatonin* (252.27 g) must be used four moles of adenosine (267.26 g).

From the above disclosure it should be apparent that the invention fully achieves the intended objects.

While the invention has been disclosed and illustrated with reference to some embodiments thereof, it should be apparent that the disclosed embodiments are susceptible to several modifications and variations all of which will come within the spirit and scope of the invention, as defined in the accompanying claims.

We claim:

1. The method of solubilizing [melatonine] *melatonin* in water which consists of mixing [melatonine] *melatonin* with adenosine in a ratio of one mole of [melatonine] *melatonin* to four moles of adenosine whereby a water soluble product is obtained.

*2. A method of preparation of melatonin having a high degree of purity which consists of the steps of:*

*a) reacting potassium phthalimide with dibromopropane, whereby 3-bromopropylphthalimide is obtained;*

*b) reacting 3-bromopropylphthalimide from step a) with acetoacetic ester in the presence of sodium ethoxide whereby ethyl 2-acetyl phthalimido-pentanoate is obtained;*

*c) reacting said ethyl 2-acetyl phthalimido pentanoate from step b) with the diazonium salt of p-anisidine whereby 2-carboxyethyl 3-(2-phthalimidoethyl) 5-methoxy indole is obtained;*

*d) reacting said 2-carboxyethyl 3-(2-phthalimidoethyl) 5-methoxy-indole from step c) first with sodium hydroxide and then with sulfuric acid whereby crude 5-methoxy-tryptamine is obtained;*

*e) reacting said crude 5-methoxy-tryptamine from step d) with hexamethyl disilazane to obtain a mixture of mono- and disubstitution products and hydrolyzing said mixture with aqueous methanol to obtain essentially pure 5-methoxy-tryptamine;*

*f) reacting said essentially pure 5-methoxy-tryptamine from step c) with acetic anhydride to obtain crude melatonin and purifying said crude melatonin by chromatography on silica gel and first eluting with methylene chloride followed by eluting with methylene chloride and acetone to obtain a solution, concentrating said methylene chloride and acetone solution to obtain a solid and recrystallizing said solid whereby purified melatonin is obtained.*

*3. The method according to claim 2 wherein said step d) is carried out by refluxing at 135° C. for 2½ hours until complete solution is obtained, then adding a 20% (v/v) $H_2SO_4$ solution and further refluxing for four hours.*

*4. The method according to claim 3 wherein after refluxing with said 20% sulfuric acid, the solution is cooled to let phthalic acid precipitate and filtering off said phthalic acid.*

*5. The method according to claim 4 wherein after said phthalic acid is filtered off, sodium hydroxide is added and crude 5-methoxytryptamine is extracted with methylene dichloride.*

*6. The method according to claim 2 wherein said step f) is carried out by refluxing for 12–14 hours said crude 5-methoxytryptamine with hexamethyl-disilazane, to obtain the mono and di-silyl substitution products, then distilling the solution under normal pressure so as to recover excess hexamethyl disilazane and hydrolyzing the silyl substitution products with aqueous methanol whereby essentially pure 5-methoxytryptamine is provided.*

* * * * *